United States Patent [19]

Card

[11] Patent Number: 4,641,651

[45] Date of Patent: Feb. 10, 1987

[54] CARTILAGE PUNCH AND MODIFIED PROSTHESIS IN TYMPANOPLASTY

[76] Inventor: George W. Card, P.O. Box 808, Goodlettsville, Tenn. 37072

[21] Appl. No.: 534,719

[22] Filed: Sep. 22, 1983

[51] Int. Cl.$^4$ .............................................. A61B 17/32
[52] U.S. Cl. ...................................... 128/305; 623/10
[58] Field of Search ....................... 128/753, 754, 305; 623/10

[56] References Cited

U.S. PATENT DOCUMENTS

| | | | |
|---|---|---|---|
| 1,188,429 | 6/1916 | Farrow | 30/358 |
| 3,191,188 | 6/1965 | Mercandino et al. | 3/1 |
| 3,608,544 | 9/1971 | Schnepper | 128/2.R |
| 3,692,020 | 9/1972 | Schied | 128/2 B |
| 3,701,352 | 10/1972 | Bosworth | 128/305 |
| 3,776,237 | 12/1973 | Hill et al. | 128/305 |
| 3,835,860 | 9/1974 | Garretson | 128/310 |
| 3,909,852 | 10/1975 | Homsy | 3/1.9 |

FOREIGN PATENT DOCUMENTS 2457862 7/1975 Fed. Rep. of Germany ...... 128/753

*Primary Examiner*—Michael H. Thaler
*Attorney, Agent, or Firm*—Holman & Stern

[57] ABSTRACT

An ossicular replacement prosthesis is configured to have its tympanic membrane-facing end self-attached to a cartilage plug forced there against. Self-attachment is achieved either by a prosthesis projection penetrating the plug, a prosthesis portion enclosing at least part of the plug, or adhesive attachment between the plug and prosthesis. A cartilage punch is provided which removes a cartilage plug of uniform thickness from a patient's tragus, retains the plug after removal and then forcefully urges the plug against the prosthesis to effect self-attachment. The punch includes a reciprocatable annular cutting member and a stage surface. Tragal cartilage is inserted between the cutting member and the stage, and the cartilage plug is cut and retained in the cutting member by forcing the cutting member toward the stage to pierce the tragel cartilage. The prosthesis is then placed on the stage so that the retained cartilage plug can be forced thereagainst by again translating the cutting member toward the stage.

12 Claims, 55 Drawing Figures

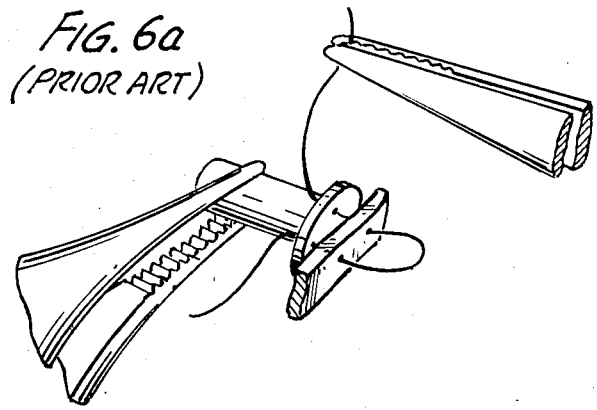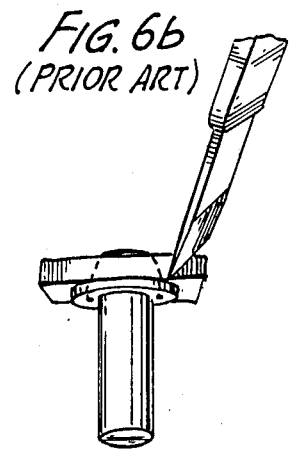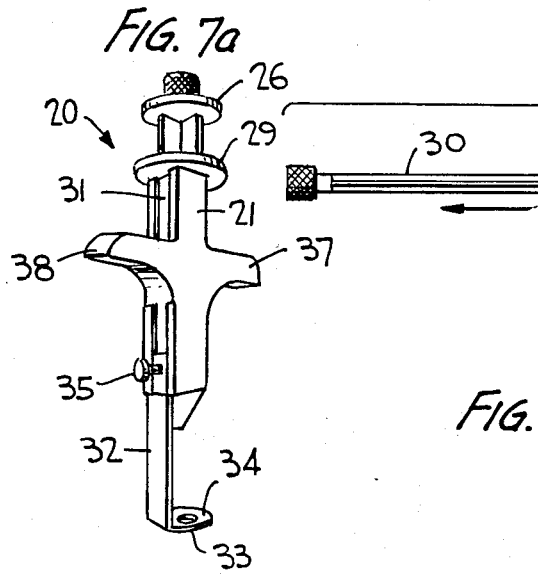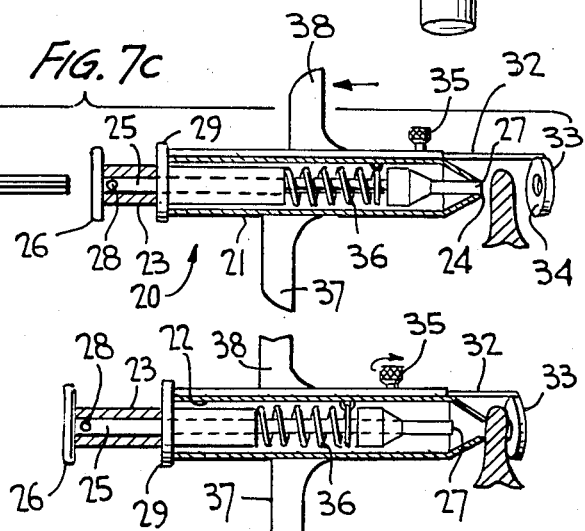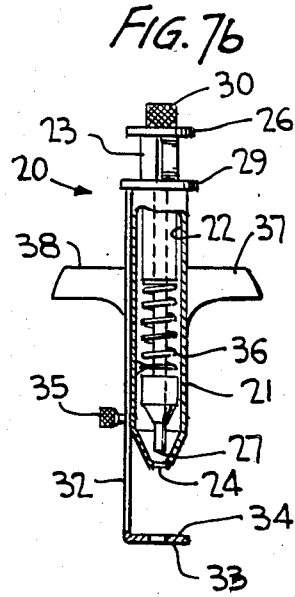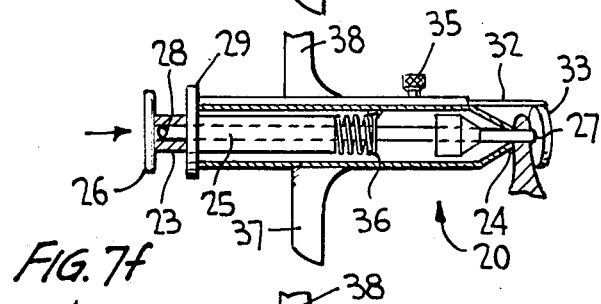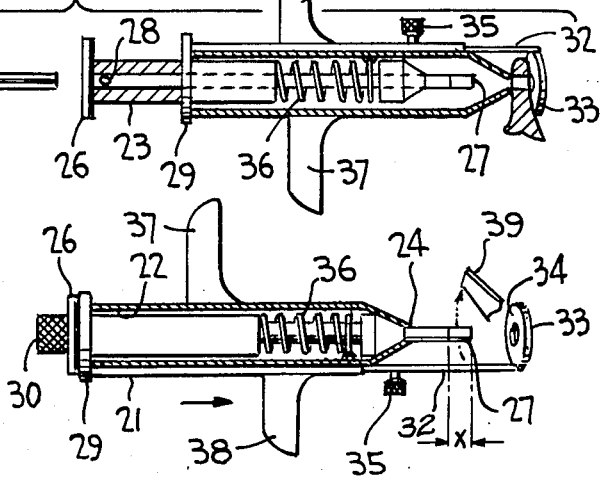

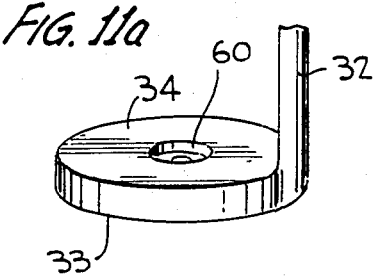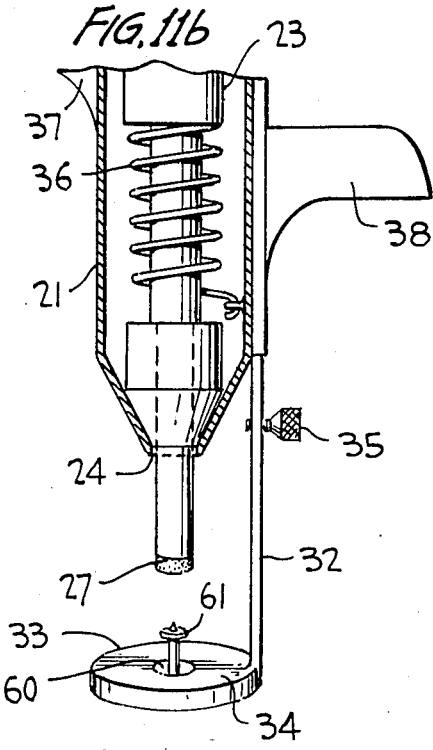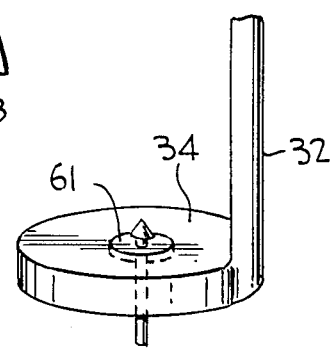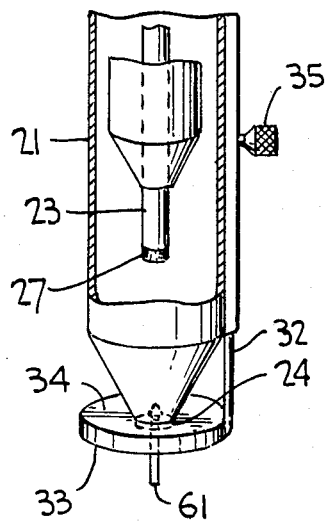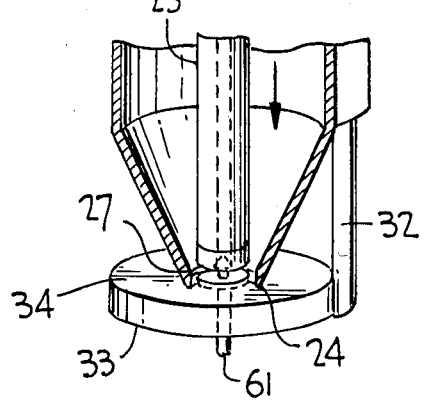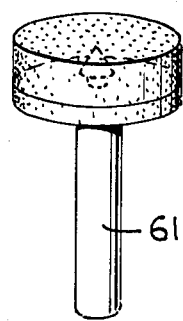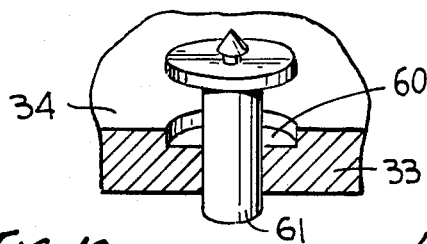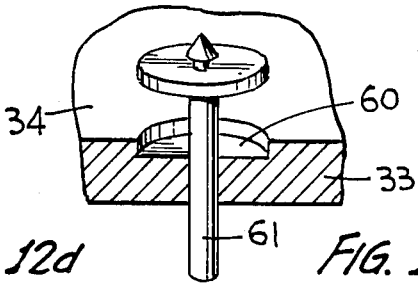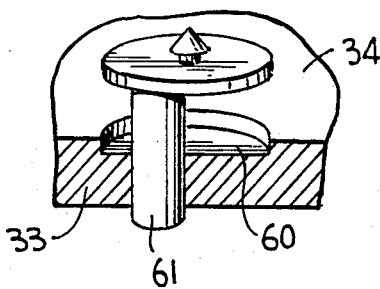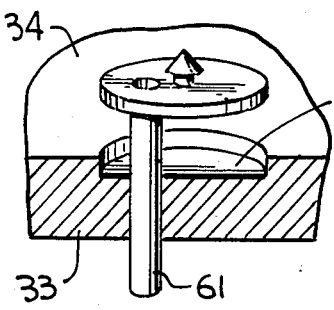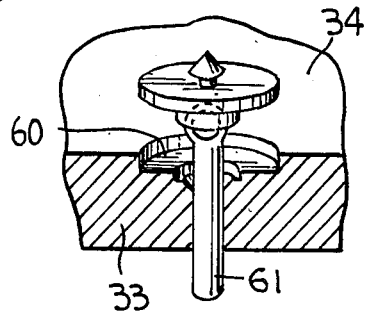

CARTILAGE PUNCH AND MODIFIED PROSTHESIS IN TYMPANOPLASTY

BACKGROUND OF THE INVENTION

1. Technical Field

The present invention relates to tympanoplasty, or the surgical reconstruction of the middle ear which restores or replaces the sound conducting mechanism. More particularly, the present invention relates to an improved method for preparing an ossicular replacement prosthesis, an improved ossicular replacement prosthetic device and a punch mechanism for removing tragal cartilage and applying the removed cartilage to the prosthetic device before the device is implanted in a patients ear.

2. Discussion of the Prior Art

Under normal circumstances, sound waves which strike the tympanic membrane (i.e. the ear drum) are transmitted through the ossicular chain of the middle ear (i.e. the malleus, the incus and the stapes) to a membrane which is stretched across the oval window of the inner ear. In this regard, reference should be made FIG. 1 of the accompanying drawings wherein a drawing of the inner ear is provided to facilitate an understanding of the structure involved. Behind the oval window membrane is fluid which fills the cochlea of the inner ear where the transmitted vibrations are translated into neural impulses. Sound transmission through the ossicular chain can become interrupted or non-functional due to a variety of diseases or injuries to the middle ear. Surgical reconstruction of the middle ear to restore or replace the sound conductive mechanism therethrough is called tympanoplasty. In cases where portions of the ossicles have become erroded, lost or otherwise non-functional, a plastic prosthetic device may be placed between the tympanic membrane and the head or footplate of a mobile stapes. An example of such prosthetic device may be found in U.S. Pat. No. 3,909,852 (Homsy). If the footplate is not mobile, the prosthetic device may be implanted between the drum and a graft placed over a drilled-out or fenestrated footplate. In either case, the ultimate goal is the restoration of the sound conduction function from the tympanic membrane to the oval window by means of a prosthetic device which replaces some or all of the ossicles. In FIG. 4a there is illustrated a typical prior art prosthetic device 10 implanted between the tympanic membrane and the head of the stapes. In FIG. 4b a typical prior art prosthetic device 11 is shown implanted between the tympanic membrane and the footplate of the stapes.

Ossicular replacement prosthetic devices take a variety of forms and are selected for implantation in accordance with the nature of the pathology and anatomical peculiarities of the patient. The present invention relates to only two types of such prosthetic devices, namely: the total ossicular replacement prosthesis (TORP) and the partial ossicular replacement prosthesis (PORP). The TORP, as its name implies, replaces the entire ossicular chain and fits between the tympanic membrane and the footplate (or fenestrated footplate) of the stapes, such as the prosthetic device 11 of FIG. 4b. This prosthetic device 11 is illustrated in greater detail in FIG. 2b and is shown to include a cylindrical shaft portion 14 terminating at one end in a circular flange 15 which faces the typanic membrane when the prosthesis is implanted. The opposite end of shaft 13 rests against the foot plate of the stapes when implanted. The PORP fits between the tympanic membrane and the head of a functioning stapes as illustrated by prosthetic device 10 illustrated in FIG. 4a. Prosthetic device 10 is illustrated in greater detail in FIG. 2a and includes a shaft 17 which terminates at its tympanic membrane-facing end in a flange 19 similar in configuration to flange 15 of prosthetic device 11. The opposite end of shaft 17 is provided with a generally cylindrical part extending longitudinally of the shaft so as to be able to receive the head of the functioning stapes. Each of prosthetic devices 10 and 11 take a variety of more specific configurations such as illustrated in FIGS. 3a through 3h, depending upon the particular anatomical features of the patient. The devices illustrated in FIGS. 3a, 3b, 3c and 3d represent PORP devices; the prosthetic devices illustrated in FIGS. 3e, 3f, 3g and 3h represent TORP devices. All of these prosthetic devices are typically constructed from a plastic material, or combination of plastic materials, that can be readily tolerated by the human body. Some of these plastics are porous and purposely designed to promote tissue ingrowth in order to stabilize the implant, much in the manner described in the aforementioned Homsy Patent. In all instances, however, the material employed must be capable of conducting sound from the tympanic membrane to the head or foot plate of the stapes.

A major problem associated with the utilization of the prosthetic devices illustrated in FIGS. 3a through 3h is the tendency toward rejection and subsequent extrusion (or perforation) of the implant when the plastic surface of the prosthesis comes into contact with the tympanic membrane or a graft which replaces this membrane. It has been found, in the prior art, that this problem can be alleviated by placing a thin slice of cartilage between the prosthesis and the tympanic membrane. This is illustrated in FIG. 5a for the PORP device and in FIG. 5b for the TORP device. In order to obtain this cartilage a surgeon must first make an incision in the leading edge of the tragus to expose the cartilage and its outer covering, the perchondrium. A piece of tragus is then removed with a scalpel making sure that the perchondrium is left intact. The cartilage is then trimmed and sewn onto the prosthesis as illustrated in FIG. 6a.

The cartilage is sewn onto the prosthesis in a manner which will bring the perichondrium of the finished implant in touch with the tympanic membrane. The cartilage is then trimmed to fit the dimensions of the flange.

This trimming procedure is illustrated in FIG. 6b and the final prosthesis, with the properly trimmed slice of cartilage, is illustrated in FIG. 6c.

There are numerous problems associated with the technique described above for obtaining the tragal cartilage and attaching it to the prosthesis. Since the procedure is performed by hand, it is a relatively time-consuming process which requires considerable dexterity on the part of the surgeon. In addition, although this technique is preferable to methods which do not use cartilage, the end product still interposes suture material between cartilage and the tympanic membrane or ear drum which could lead to rejection and extrusion. Further, since is is trimmed with a scalpel, the resulting cartilage plug has sharp edges which may lead to perforation of the ear drum. Finally, the suture employed for this procedure does not dissolve and consequently is always in contact with the drum, thereby promoting infection and utilmate extrusion.

OBJECTS AND SUMMARY OF THE INVENTION

It is therefore an object of the present invention to improve tympanoplastic techniques so as to eliminate the disadvantages and problems set forth above.

It is another object of the present invention to provide an improved method for obtaining a cartilage plug from a patient's tragus and applying that plug to a prosthetic device for implantation into the middle ear.

A further object of the present invention is to provide a cartilage punch capable of simply and effectively removing tragel cartilage in the form of a plug having uniform thickness, retaining that plug after removal, and then applying the plug to a prosthetic device.

Another object of the present invention is to provide an improved prosthetic device for use in replacing some or all of the ossicles in a patient's middle ear and which is capable of self-attachment to a cartilage plug without the use of suture material, or the like.

One of the objects of the present invention is to provide a method for preparing an ossicular replacement prosthesis in a patient's ear by removing a plug of tragal cartilage from the patient's ear with a hollow reciprocal cutting tool by forcefully translating the cutting tool toward a stage when the tragal cartilage is disposed between the cutting tool and the stage, retaining the removed plug in the cutting tool, placing the prosthesis on the stage, forcefully urging the retained cartilage plug against the prosthesis on the stage, and attaching the prosthesis to the plug in response to the forceful urging of the plug against the stage.

It is another object of the present invention to provide an ossicular replacement prosthesis adapted for in vivo implantation between the tympanic membrane and oval window of a patient's ear comprising a surface adapted to have a cartilage plug secured thereto to be disposed between the surface and the patient's tympanic membrane, and an attachment means for engaging the cartilage plug in response to forceful application of the plug to the prosthesis in a direction generally perpendicular to the prosthesis surface.

A still further object of the present invention is to provide a cartilage punch for exising a cartilage plug of uniform thickness from a cartilage mass in vivo and including a housing member with an elongated passage defined therein and a cutting opening at one end thereof, a cutting plunger secured in the housing member for longitudinal reciprocating movement in the elongated passage, wherein the cutting plunger has an annular cutting end disposed to to be selectively projected out through the cutting end of the housing member, an anvil secured to the housing member and having a stage surface oriented generally perpendicular to the longitudinal reciprocating movement of the cutting plunger, the stage surface being translatable in a direction parallel to the direction of reciprocating movement of the plunger so as to selectively position the stage surface with respect to the housing, and means for selectively forcefully translating the cutting plunger toward the cutting opening to force the annular cutting end of the plunger through the cutting opening so as to cut a cylindrical plug of cartilage and retain that plug within the annular cutting end.

In accordance with the present invention, a cartilage punch is provided in a syringe-like configuration with a hollow core terminating in an annular cutting tip. An anvil assembly includes a stage surface disposed externally of the housing and toward which the cutting tip is selectively translatable. The stage surface can be adjusted at selected distances from the housing to permit insertion of the tragal cartilage mass between the housing and stage surface. A cartilage plug is obtained from the inserted tragal cartilage mass by forcing the cutting tip toward the stage surface so as to penetrate the tragal cartilage mass and cut a plug therefrom which is retained within the annular cutting tip. Retraction of the cutting tip permits removal of the cartilage mass, after which time a prosthetic device may be inserted onto the stage surface for eventual forceful engagement between the retained cartilage plug and the flange or similar portion of the prosthetic device.

A core rod is provided and is insertable into the hollow core of the cutting member in order to extrude unnecessary cartilage portions of the retained plug, which portions can then be removed by means of a scalpel, or the like. The tip of this rod may also be employed to stabilize the remaining cartilage plug when it is forcefully pressed against the prosthetic device for attachment thereto.

An improved prosthetic device is provided whereby the flange or like surface thereof attaches directly to the cartilage plug in response to the forceful urging of that plug against the prosthetic device. Engagement of the plug at the prosthetic device may be effected by proejctions which penetrate the cartilage plug, projections which partially enclose the cartilage plug or by adhesive attachment of the cartilage plug to the prosthetic device. The stage surface of the cartilage punch is contoured to receive the prosthetic device to facilitate transfer of the cartilage plug to that device.

BRIEF DESCRIPTION OF THE DRAWINGS

The above and still further object, features and advantages of the present invention will become apparent upon consideration of the following detailed description of specific embodiments thereof, especially when taken in conjunction with the accompanying drawings wherein like numbers in the different figures represent the same elements, and wherein:

FIGS. 6a through 6c illustrate a prior art prosthetic device and the method of attachment thereto of a cartilage slice in accordance with the prior art;

FIG. 7a is a view in perspective of a cartilage punch constructed in accordance with the present invention;

FIG. 7b is a plan view in partial section of the cartilage punch of FIG. 7a;

FIG. 7c is a view similar to FIG. 7b but showing the cartilage punch deployed so as to receive tragel cartilage prior to a cutting procedure;

FIG. 7d is a view similar to FIG. 7b showing tragel cartilage properly inserted into the cartilage punch immediately prior to a cutting procedure;

FIG. 7e is a view similar to FIG. 7b showing the cartilage punch in the process of cutting a cartilage plug from the inserted tragel cartilage;

FIG. 7f is a view similar to FIG. 7b showing the cartilage punch after a plug of cartilage has been removed from the tragel cartilage mass;

FIG. 7g is a view of the cartilage punch of FIG. 7b showing a trimming operation of the removed cartilage plug after an excess portion of the plug has been extruded from the cutting member;

FIGS. 11a through 11f show sucessive stages in the procedure whereby a prosthetic device in accordance with the present invention is inserted into the cartilage punch assembly, and a cartilage plug previously cut and retained is secured to the prosthetic device; and FIGS. 12a through 12e are respective views in section of different configurations of the stage surface of the cartilage punch of the present invention arranged to receive differently configured ossicular replacement prosthetic devices of the present invention.

DESCRIPTION OF THE PREFERRED EMBODIMENTS

Figure 1:
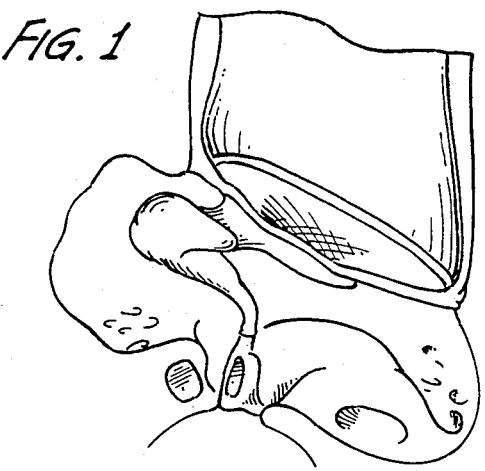
FIG. 1 is a diagrammatic illustration of a human inner ear.
Figure 2A:
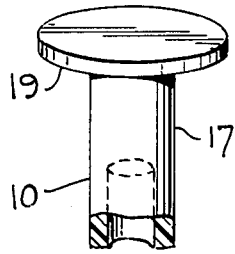
FIGS. 2a and 2b are views in perspective of prior art partial ossicular replacement prosthesis and total ossicular replacement prosthesis devices, respectively.
Figure 2B:
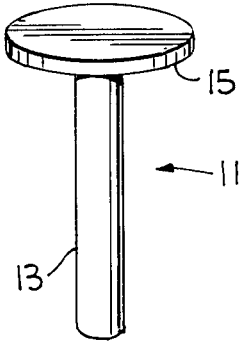
Figure 3A:
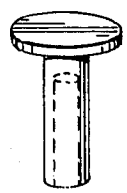
FIGS. 3a through 3h inclusive, are respective views in perspective of prior art ossicular replacement prosthetic devices.
Figure 3B:
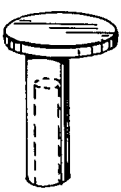
Figure 3C:
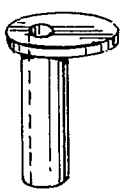
Figure 3D:
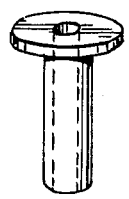
Figure 3E:
Figure 3F:
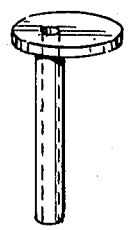
Figure 3G:
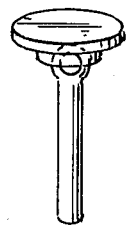
Figure 3H:
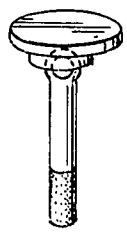
Figure 4A:
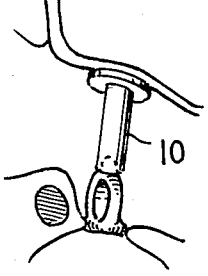
FIGS. 4a and 4b are diagramatic representations of prior art ossicular replacement prosthetic devices impalnted in the middle ear of a patient.
Figure 4B:
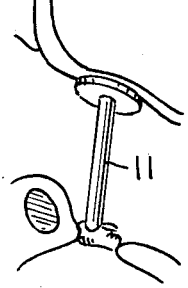
Figure 5A:
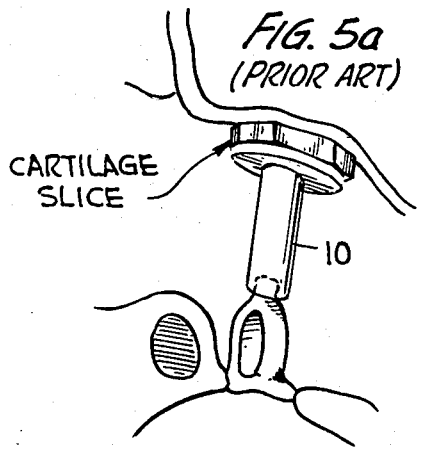
FIGS. 5a and 5b are views similar to FIGS. 4a and 4b, respectively, but showing a prior art cartilage slice attached to the prior art prosthetic devices to abut the tympanic membrane when implanted.
Figure 5B:
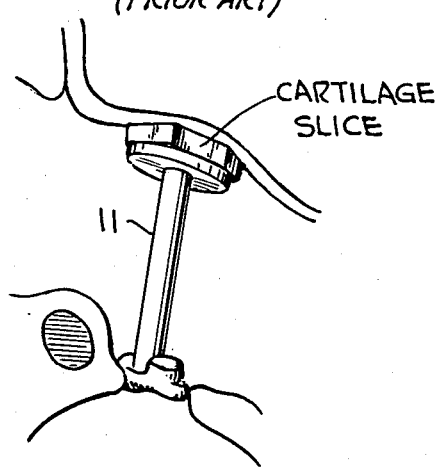

Referring specifically to FIGS. 7a and 7b of the accompanying drawings, a cartilage punch 20, constructed in accordance with the principles of the present invention, takes the form of a syringe-like device having a housing member 21 with an elongated bore or passage 22 extending entirely therethrough. Housing member 21 has an opening at its rear or proximal end which communicates with elongated passage 22 so that a plunger member 23 can be received in the passage. The opposite end of the housing member 21 is provided with a cutting opening 24 which also communicates with the elongated passage 22. Plunger 23 is selectively translatable longitudinally within the elongated passage 22 and includes an internal longitudinally-extending hollow core 25 extending between its longitudinal ends. One end of the plunger 23, namely the proximal end, includes an enlarged diameter flange 26 for suitable engagement by a user's thumb in forcing the plunger into the housing member 21. The opposite end of the plunger terminates in an annular cutting tip 27 which, by virtue of the selective translation of plunger 23 in passage 22, can be selectively projected out from and withdrawn into passage 22 at cutting opening 24 in the housing member. A vent opening is provided in the periphery of plunger 23 to permit the hollow interior 25 of plunger 23 to communicate with ambient air. Vent opening 28 is preferably located, in the manner illustrated, adjacent the actuator flange 26. A similar flange 29 is provided at the proximal end of housing member 21 to serve as a stop by abutting flange 26 in the fully inserted position of the plunger 23. A core rod 30 is selectively insertable longitudinally into the hollow interior region 25 of plunger 23. As will be described subsequently in greater detail, the purpose of core rod 30 is twofold: first, the core rod is used to extrude excess portions of cartilage which have been cut and retained by cutting tip 27; second, the core rod stabilizes the retained cartilage when the cartilage is being attached to a prosthetic device.

An anvil or stage assembly for the cartilage punch includes a track assembly extending longitudinally along one side of housing member 21. An elonagated runner 32 is slidably engaged in the track assembly 31 and includes a stage member 33 secured at its distal end. Stage member 33 is disposed forwardly of the cutting opening 24 of housing member 21 and is displaceable at variable distances from that cutting opening by sliding runner 32 in the track assembly 31 to the desired position. A stage surface 34 of the stage member 33 is oriented substantially perpendicular to the direction of longitudinal motion of plunger 23 in housing 21 so as to squarely face the cutting opening 24. A set screw 35 is secured to the runner 32 so as to be extendable transversely therethrough into the track assembly 31 for locking the runner in place at various locations along the length of the housing.

The plunger is normally biased in its retracted position wherein cutting tip 27 is withdrawn into the housing. This bias is effected by a spring 36 having one end secured to the housing and the other end secured to the plunger internally of the housing and having its intermediate portion helically wound about the plunger.

The housing is provided with a grip 37 extending radially outward from the housing at one side thereof which is opposite the side on which the track assembly is defined. A corresponding grip or trigger member 38 is secured to runner 32 to facilitate translation thereof in the track 31. In addition, grip members 37 and 38 facilitate the grabbing of the housing with the user's fingers while the plunger is depressed into the housing by means of the user's thumb applied to flange 26, much in the manner of the actuation of a syringe.

In operation of the cartilage punch, the core rod 30 is first removed from the hollow interior 25 of plunger 23 in the manner illustrated in FIG. 7c. In this regard, the core rod 30 is exteriorly threaded at a location adjacent its proximal end so as to engage an internally threaded portion of flange 26. This threaded engagement is disconnected in order to remove the rod. Once rod 30 has been removed, stage member 33 is extended relative to cutting opening 24 by loosening the set screw 35 and sliding runner 32 as necessary in the track assembly 31. The tragal cartilage is then inserted between the cutting opening and the stage surface 34. With the tragal cartilage properly positioned as aforesaid, runner 32 is retracted in slide member 31 to tightly engage opposite sides of the tragal cartilage mass between the cutting opening 24 and the stage surface 34 as illustrated in FIG. 7b. The set screw is then tightened to maintain this engagement of the tragal cartilage mass. With the cartilage mass thus set in the punch, the plunger 23 is pushed to force the annular cutting end 27 of the plunger out through cutting opening 24 toward surface 34. As a result, the annular cutting end 27 penetrates the tragal cartilage mass to cut a plug from the cartilage which is forced inside the forward end of the hollow interior end 27 of the plunger as illustrated in FIG. 7e. Once the cartilage has been punched, the plunger is released so as to be forced backward by the urging of bias spring 36 to the position illustrated in FIG. 7f.

The resulting cartilage plug which is equal in length to the thickness of the tragal cartilage is entirely retained in the bore of the cutting assembly As illustrated in FIG. 7g, set screw 35 is then released to permit the runner 32 to be extended to its maximum displacement within track assembly 31 so that the spacing between the cutting opening 24 and stage 33 is substantially at a maximum. Rod 30 is then inserted into the hollow interior of the plunger member 23 and the plunger is once again forcefully urged through the housing member so as to project cutting end 27 out through cutting opening 24. The core rod 30 is used to project excess cartilage out from the exposed cutting end 27.

At its fullest insertion, rod 30 extends into hollow core 25 to fullest insertion, rod 30 extends into hollow core 25 to within a predetermined distance "x" of the cutting edge of end 27, so that the slug of cartilage remaining after trimming has a length equal to "x".

This excess cartilage is trimmed by means of a scalpel 40 or the like, so that all that remains is the portion of the cartilage plug retained within the hollow interior 25 of the plunger 23. The trimming operation is diagramatically illustrated in FIG. 7g. The retained plug is then ready for attachment to a prosthetic device in a manner described herein below.

Figure 8A:
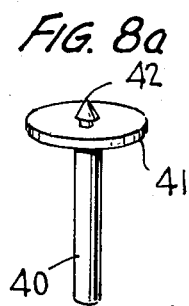
FIGS. 8a, 8b, 8c, 8d, 8e, 8f, 8g, 8h, 8i, 8j, 8k, 8l, 8m, 8n and 8o are respective view in perspective of ossicular replacement prosthetic devices constructed in accordance with the present invention.

In order to eliminate the disadvantages and problems described above as being associated with suturing the cartilage plug to the ossicular chain prosthetic device, the flange of that device is modified in accordance with the present invention so that the plug will attach directly to the flange upon being urged against the flange. Since the modification of the prosthetic device affects only the flange portion thereof, the self-attachment feature of the present invention is applicable to both the TORP and PORP types of prosthetic devices. The devices illustrated in FIGS. 8a through 8i illustrate one general form of prosthetic devices whereby the attachment of the cartilage plug to the flange is effected by means of a member secured to the flange (or formed integrally therewith) and arranged to penetrate and engage the cartilage plug when the plug is urged against the flange. Referring specifically to FIG. 8a, an ossicular replacement prosthetic device includes a stem or shaft portion 40 with a flange 41. The projecting attachment member is configured as a barb 42 having a shaft connected to an extending perpendicularly from the flange and terminating in a conical tip which is wider that the shaft at its proximal end but tapers to a point at its distal end.

Figure 8B:
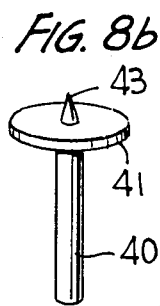
Figure 8C:
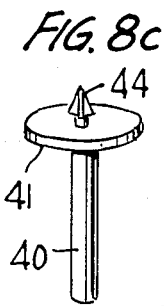
Figure 8D:
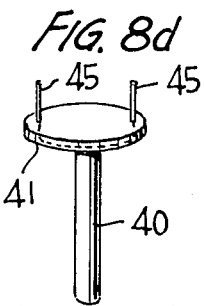
Figure 8E:
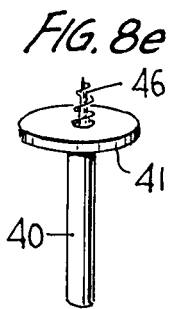
Figure 8F:
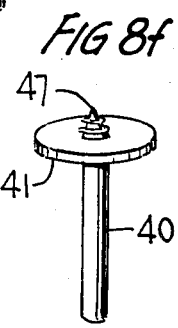
Figure 8G:
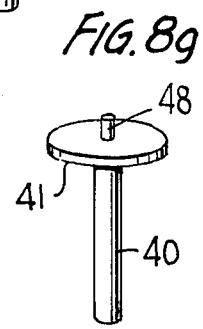
Figure 8H:
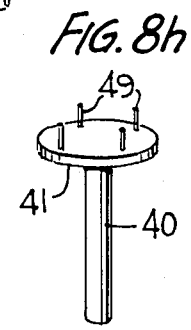
Figure 8I:
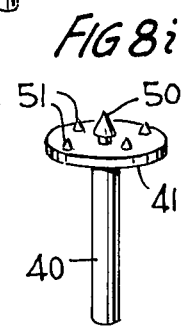
Figure 8J:
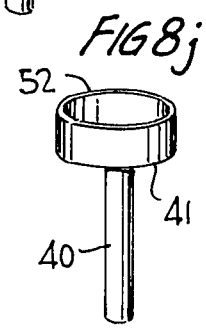

A modification of this structure may be found in FIG. 8b wherein the projecting portion is a spike or needle 83 rather than a barb 42. Another alternative embodiment is found in FIG. 8c wherein the barb 44 is shown as being bifurcated longitudinally to facilitate engagement of the cartilage plug. It should also be noted that the spike or needle of FIG. 8b may be bifurcated in a similar manner. The attachment device of FIG. 8d takes the form of a staple 45 embedded in the flange 41 and having its ends directed perpendicularly away from the flange to receive the cartilage plug. In FIG. 8e the projection takes the form of a tapered screw 46, in FIG. 8f it takes the form of a modified spike or barb 47, in FIG. 8g it takes the form of a hollow cylinder or shaft 48. FIG. 8h illustrates the projections in the form of a plurality of needles extending from the flange 41. In FIG. 8i a combination of different types of projections are illustrated such as a barb 50 and a plurality of spikes 51. It should be noted that any combination of elements which project into the plug may be employed in a similar manner.

Figure 8K:
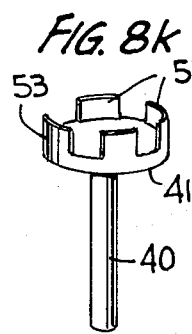
Figure 8L:
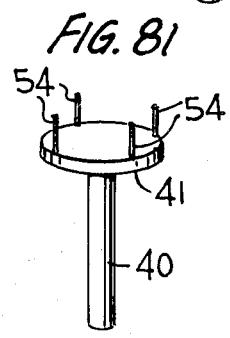
Figure 8M:
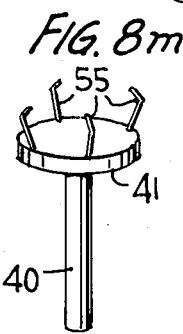

In the embodiments illustrated in FIGS. 8j through 8m, engagement of the cartilage plug is by means of a partial enclosure of the plug at the flange surface. For example, in FIG. 8j the flange 41 is illustrated as including an annular wall disposed at its periphery and projecting forwardly of the flange to receive the plug therein. Annular wall 52 may be likened to a cuff or similar such structure. In FIG. 8k a modified cuff is illustrated wherein the annular wall is segmented into equally angularly spaced portions 53 which serve to receive and engage the cartilage plug when it is forced against the flange 41. FIG. 8l illustrates an embodiment wherein the flange 41 is provided with a series of angularly spaced prongs 54 disposed at its periphery and facing away from the flange to, again, receive the cartilage plug when that plug is forced against the flange. In FIG. 8m the engaging members constitute a portion of staples or other resilient type members 55.

Figure 8N:
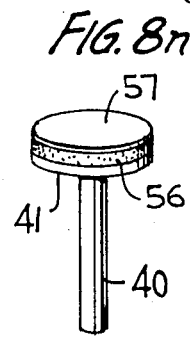
Figure 8O:
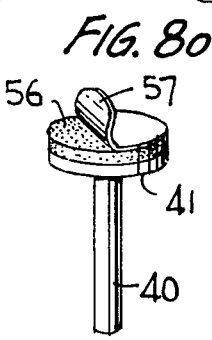

A third general category of means for attaching the cartilage plug automatically to the prosthetic device in response to forceful engagement between the plug and the prosthetic device is illustrated in FIGS. 8n and 8o. Specifically, the receiving surface of flange 41 is treated with an adhesive material 56 which, upon contact with the cartilage plug, is capable of being firmly secured to the cartilage plug. The adhesive material 56 is preferably normally covered by a protective covering 57 which would normally be peeled from the adhesive material 56 prior to attachment of the prosthetic device to the cartilage plug.

Figure 9A:
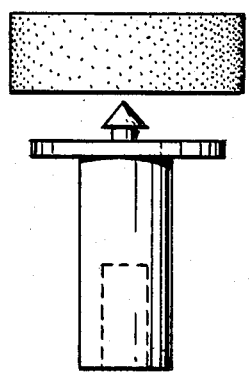
FIGS. 9a and 9b are partially diagramatic views in plan showing partial (FIG. 9a) and total (FIG. 9b) ossicular replacement prosthetic devices in conjunction with cartilage plugs to be attached thereto.
Figure 9B:
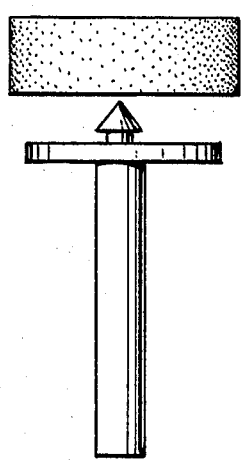
Figure 10A:
FIG. 10a is a view in perspective of a modified version of a partial ossicular replacement prosthetic device constructed in accordance with the principles of the present invention.
Figure 10B:
FIG. 10b is a total ossicular replacement prosthetic device constructed in accordance with the principles of the present invention.

Of the various embodiments illustrated in Figures 8a through 8o, the particular embodiments illustrated in FIGS. 8a through 8i, wherein the cartilage plug is penetrated by a "male" projection, offers certain advantages. More particularly, this type of attachment is purely mechanical and, therefore, the risk of physiological reaction to an adhesive is eliminated. In addition, this configuration permits reduction of the diameter of the flange, as illustrated in FIGS. 9a and 9b, so that the flange diameter is smaller than the diameter of the attached cartilage plug. This feature further minimizes the possibility of any contact between the prosthetic device and the tympanic membrane. Moreover, since the only purpose of the flange is to provide stabilization of the cartilage plug, the stabilization effected by the mechanical attachment permits elimination of the flange entirely, as illustrated in FIG. 10a, or at least a reduction in its diameter, as illustrated in FIG. 10b. For these reasons a prosthetic device utilizing a "male" penetraing element incorporated into the flange or exposed surface of the prosthetic device constitutes the preferred form of the prosthetic device in accordance with the present invention.

The procedure for attaching the cartilage plug to the prosthetic device of the present invention using the cartilage punch of the present invention is illustrated diagrammatically in FIGS. 11a through 11f. Specifically, FIG. 11a illustrates the empty stage surface 34 of stage member 33 after cartilage has been cut and retained by the cartilage punch. It is noted that a recess 60 is provided in the stage surface 34. As illustrated in FIGS. 11b and 11c recess 60 is configured to receive the prosthetic device 61 with the stem or shaft of the prosthetic device extending into the recess and, if necessary, through the stage member 33, depending upon the thickness of stage member 33. The surface of the prosthetic device to which the cartilage plug is to be secured is positioned so as to face the cutting opening 24 of the cartilage punch. With the prosthetic device 61 placed in recess 60, the runner 32 is retracted in slide member 31 so as to place the retained prosthetic device 61 adjacent cutting opening 24. At this time it is assumed that the plunger 23 is retracted within housing 21 so as not to interfere with the placing of the prosthetic device at the cutting opening. This condition is illustrated in FIG. 11d. With the prosthetic device properly positioned at the cutting opening, the plunger is depressed, as illustrated in FIG. 11e, to force the retained cartilage plug onto the prosthetic device 61 where it is automatically retained in accordance with the present invention as described hereinabove. FIG. 11f illustrates the finished prosthetic product, after it has been removed from the cartilage punch, with the cartilage plug secured thereto.

It should be noted that the stage member 33 of the cartilage plug can be adapted to be configured to receive any variety of prosthetic device configurations. FIGS. 12a through 12e illustrate a variety of different configurations for recess 60 so as to accommodate a corresponding variety of different prosthetic device configurations. In each of FIGS. 12a through 12e the recess 60 includes a bore extending entirely through the stage member 33 so as to permit the entire shaft of the prosthetic device 61 to extend through and beyond the stage member. It should be noted that the stage member may be provided with sufficient depth so that the stem or shaft of the prosthetic device need not extend entirely therethrough, whereby the recess 60 would not extend entirely through the stage member.

The entire procedure for cutting and retaining the cartilage plug in the cartilage punch and then attaching the cartilage plug to the prosthetic device takes no more than a few minutes and results in an attached cartilage plug with a diameter appropriate for the prosthesis chosen for implantation. The plug has no suture material between the perichondrium and the tympanic membrane and has no sharp edges. These factors lessen the change of extrusion or perforation. The process of the present invention has the added advantage of taking only a negligable portion of the tragel cartilage from the patient, thereby minimizing trauma to the patient.

The combination of the cartilage punch and ossicular replacement prosthesis of the present invention, employed in the method of the present invention, offers considerable advantages over the prior art surgical procedures for obtaining a suitable prosthesis with a cartilage plug attached to the flange. For example, the automatic cutting, retaining and applying of the plug by the punch cuts down on the amount of work, skill and time required to perform the procedure by hand. In addition, as noted above, no suture material or other foreign substance is interposed between the perichrondrium and tympanic membrane. Further, the resulting cartilage plug corresponds to the dimensions of the flange of the prosthetic device and has no sharp edges which could lead to perforation of the ear drum. It should also be noted that the combination of the cartilage punch and the modified prosthetic device allows a reduction in flange diameter to further ensure against contact of the prosthetic device and the tympanic membrane. Moreover, since in this process the flange only serves to stabilize the cartilage plug, it may be possible to eliminate the flange entirely. Finally, much less cartilage is removed from the tragus of the patient, thereby lessening the trauma to the patient in obtaining the necessary cartilage plug.

While I have described and illustrated specific embodiments of my invention, it will be clear that variations of the details of construction which are specifically illustrated and described may be resorted to without departing from the true scope and spirit of the invention as defined in the appended claims.

What is claimed is:

1. A cartilage punch for excising a cartilage plug of uniform thickness from a cartilage mass in vivo in combination with a prosthetic device, comprising:
   a housing member having an elongated passage therein and a cutting opening at one end thereof, said elongated passage terminating at said cutting opening;
   a prosthetic device having a surface adapted to have a cartilage plug secured thereto;
   a cutting plunger secured in said housing member for longitudinally reciprocating movement in said elongated passage, said cutting plunger having an annular cutting end disposed to be selectively projected out through said cutting opening end including a hollow interior communicating with said cutting end;
   an anvil means fixed to said housing member and including a stage surface oriented generally perpendicularly to a direction corresponding to said longitudinal reciprocating movement of said cutting plunger, said anvil means further comprising an extension means for selectively adjustably translating said stage surface in a direction generally parallel to said direction to selectively increase and decrease spacing between said stage surface and said cutting opening to thereby permit insertion and removal of said cartilage mass in said spacing;
   a means for selectively forcefully translating said cutting plunger toward said cutting opening to force said annular cutting end through said cutting opening and toward said stage surface through the cartilage mass disposed on said space;
   whereby a plug of cartilage is cut by said cutting end and substantially completely forced into said hollow interior portion of said cutting plunger by the forceful translation of said cutting plunger toward said stage surface wherein a thickness dimension of the plug conforms to an interior dimension of said hollow interior portion taken in a direction generally transverse to said longitudinally reciprocating movement;
   said stage surface being recessed in a predetermined configuration to stably receive said prosthetic device with said surface of said prosthetic device facing said cutting opening, whereby said plunger can be selectively extended from said elongated passage to bring said surface of said prosthetic device into contact with the cartilage plug disposed in the hollow interior of said cutting plunger;

said prosthetic device including an attachment means disposed at said surface of said prosthetic device for mechanically engaging the cartilage plug.

2. The cartilage punch according to claim 1 further comprising a means for selectively initially partially extruding the cartilage plug from said hollow interior portion of said cutting end such that a predetermined length of the cartilage plug remains within said hollow interior portion.

3. The cartilage punch according to claim 2 wherein said means for selectively extruding comprises an elongated rod member having a free end and a stop means for limiting insertion into said hollow interior portion, said elongated rod member having a predetermined length relative to said cutting end such that, at full insertion of said elongated rod member into said hollow interior portion, said free end being disposed such that said free end is spaced from said cutting end by a spacing means by a distance equal to said predetermined length of the cartilage plug.

4. The cartilage punch according to claim 1 wherein said anvil means further comprises an adjustable means for selectively securing said extension means relative to said housing at any translational position within a predetermined range of positions so as to correspondingly secure said stage surface at any desired spacing relative to said cutting opening within a corresponding range of spacings.

5. The cartilage punch according to claim 1 wherein said extension means comprises a track disposed in said housing member extending parallel to said dimension of reciprocating movement, and a runner secured in said track for slidable longitudinal movement therein, and wherein said stage surface is secured to and projects generally transversely from said runner in front of said cutting opening.

6. The cartilage punch according to claim 5 further comprising means for selectively applying a transverse force to said slide to compress the runner against said track and preclude said slidable longitudinal movement of said runenr in said track.

7. The cartilage punch according to claim 1 wherein said housing member, said cutting plunger, and said means for forcefully translating said cutting plunger constitute an assembly in which said housing member is open at an end opposite said cutting end and wherein said cutting plunger is selectively insertable into said housing member and forcefully projected through said cutting opening from said opposite end.

8. The cartilage punch according to claim 1 further comprising a bias means for continuously urging said cutting plunger away from said cutting opening in said elongated passage and toward a limit position wherein said cutting end is withdrawn into said elongated passage.

9. The cartilage punch according to claim 1 wherein said attachment means comprises means for penetrating said plug in a dimension parallel to the dimension of reciprocating movement of said cutting plunger.

10. The cartilage punch according to claim 1 wherein said attachment means comprises a means for at least partially enclosing said cartilage plug at said surface.

11. The cartilage punch according to claim 1 wherein said attachment means comprises a means for adhesively securing said cartilage plug to said one surface.

12. The cartilage plug according to claim 1 wherein said prosthetic device is an ossicular replacement device.

* * * * *